United States Patent [19]

Leonard

[11] 4,031,196

[45] June 21, 1977

[54] PREPARING AQUEOUS ALKALINE SLURRY OF THALLIC OXIDE

[75] Inventor: John J. Leonard, Springfield, Pa.

[73] Assignee: Atlantic Richfield Company, Los Angeles, Calif.

[22] Filed: Aug. 24, 1976

[21] Appl. No.: 717,309

Related U.S. Application Data

[62] Division of Ser. No. 579,758, May 22, 1975, abandoned.

[52] U.S. Cl. .......................... 423/624; 260/348.56; 260/593 R
[51] Int. Cl.$^2$ ........................................ C01G 15/00
[58] Field of Search ................... 423/624, 122, 127

[56] References Cited

UNITED STATES PATENTS 3,048,636   8/1962   Grinstead .......................... 423/624

FOREIGN PATENTS OR APPLICATIONS

| 49-13104 | 2/1974 | Japan | 423/624 |
| 44-658 | 1/1969 | Japan | 423/624 |
| 1,100,806 | 1/1968 | United Kingdom | 423/624 |
| 201,353 | 10/1967 | U.S.S.R. | 423/624 |

OTHER PUBLICATIONS

Berry, "Journal of the Chemical Soc.", vol. 123, 1923, pp. 1109–1114.

Mellor, "Comprehensive Treatise on Inorganic & Theoretical Chemistry", vol. 5, 1946, pp. 430–436.
Obara et al., "Chemical Absts.", vol. 83, 1975, abstract 34761c.

*Primary Examiner*—Herbert T. Carter
*Attorney, Agent, or Firm*—John R. Ewbank

[57] ABSTRACT

In an aqueous alkaline solution having a pH greater than 11.9, thallous isobutyrate is oxidized by air in a temperature within a range from about 90° C to about 250° C to prepare a slurry of thallic oxide from which thallic oxide can be recovered. The alkaline isobutyrate solution can be treated with carbon dioxide under pressure to form a carbonate salt and isobutyric acid, which can be solvent extracted from the aqueous system. Such isobutyric acid can be employed in a 30 percent aqueous solution at 90°–150° C to dissolve thallic oxide and to prepare thallic triisobutyrate. This aqueous solution of thallic triisobutyrate can be employed for the oxidation of an organic compound susceptible to oxidation to desirable partially oxidized organic compounds, such as the oxidation of propylene to propylene oxide. The carbonate salt can be thermally decomposed to regenerate an alkaline metal hydroxide and carbon dioxide. The availability of this novel preparation of thallic oxide makes feasible the recycling of most components, so that the thallium ion is an intermediate useful for the oxidation of an organic compound indirectly using the oxygen of air through such cyclic processing of the thallium ion.

2 Claims, No Drawings

PREPARING AQUEOUS ALKALINE SLURRY OF THALLIC OXIDE

RELATED APPLICATIONS

This is a compulsory division of copending parent Ser. No. 579,758 filed May 22, 1975, and now abandoned. Sister application Ser. No. 717,308 filed Aug. 24, 1976 is a continuation of the subject matter elected in said parent application.

FIELD OF THE INVENTION

This invention relates to the preparation of thallic oxide from an aqueous solution containing thallous ion, to the oxidation of organic compounds by aqueous solutions of thallic ion and to recycle procedures for indirectly using the oxygen of air for the oxidation of an organic compound; for example, oxidizing propylene to propylene oxide using thallium ion as the intermediate

PRIOR ART

Grinstead U.S. Pat. No. 3,048,636 and British Pat. No. 1,100,806 describe the oxidation of unsaturated organic compounds with solutions of thallic salts. There has been a long-standing demand for a process permitting such use of thallic ion for oxidation and permitting satisfactory recycling of the thallium ion and related intermediates so that the oxidation was achieved indirectly by the consumption of the oxygen from air.

SUMMARY OF THE INVENTION

In accordance with the present invention, thallic oxide is prepared by the oxidation of a thallous alkanoate in an aqueous solution having a pH greater than 11.9 by the introduction of an oxygen-containing gas into such system at a temperature range from about 90° C. to about 250° C. The thallic oxide can be recovered from the aqueous alkaline slurry and dissolved in an alkanoic acid to prepare the aqueous solution of thallic trialkanoate suitable for use in the preparation of a partially oxidized organic compound.

The nature of the invention is further clarified by reference to a plurality of examples.

EXAMPLES 1-4

A quantity of about 400 cc of aqueous alkaline solution is supplied to a titanium autoclave having a magnetic stirrer. The aqueous solution contains 0.19 molar thallous acetate. The oxygen containing gas contacts the stirred solution to oxidize the thallous ion to the thallic ion. The gas pressure was 300 psi of nitrogen and 300 psi of oxygen. The aqueous system contains the concentration of sodium necessary to obtain the indicated pH. In a series of preparations, the yield of thallic oxide was measured (the $Tl_2O_3$ being separated by filtration and its purity confirmed by analysis) to determine the effect of variations in the duration of the treatment and variations in initial pH. No measurable difference in pH occurred during the reaction. The results of this series of preparations are shown in Table 1. In Control A, the pH of the aqueous solution was only 11.5, with a significant loss in yield of $Tl_2O_3$ compared to $Tl_2O_3$ at a pH of 12.5.

Table 1

|  | molarity [NaOH] | pH | hrs. | % yield |
|---|---|---|---|---|
| Control A | 0.003 | 11.5 | 0.5 | 1.3 |

Table 1-continued

|  | molarity [NaOH] | pH | hrs. | % yield |
|---|---|---|---|---|
| Example 1 | 0.03 | 12.5 | 0.5 | 10 |
| Example 2 | 0.3 | 13.5 | 0.5 | 52 |
| Example 3 | 3.0 | 14.5 | 0.5 | 74 |
| Example 4 | 3.0 | 14.5 | 2 | 100 |

Such data show that oxygen can oxidize thallous ion to thallic ion at 150° C. at a rate of commercial interest if the pH is greater than 11.9. By a series of tests it is shown that the temperature must be maintained within a range from 90° C. to 250° C., and the initial thallium ion concentration in the aqueous composition must be at least 0.05 molar and desirably is less than 3 molar. The alkanoate ion concentration must be at least equal to the thallium ion concentration. The thallic oxide product is not merely insoluble in the reaction product, but also forms in a particle size suitable for separation by centrifuging or filtration. Such separability of a precipitate by filtration (it being herein assumed that if commercial filtration is manageable, then centrifuging is also manageable) is remarkable because hot aqueous alkaline solutions containing 3 molar sodium hydroxide at a pH such as 14.5 tend to disperse many precipitates in a colloidal form not susceptible to commercial filtration. It is sometimes advantageous to cool the reaction mixture prior to filtration, to wash the thallic oxide filter cake with dilute (e.g., pH 9) sodium hydroxide until the filtrate has a pH essentially the same as the wash liquid, and to dry the recovered thallic oxide.

EXAMPLES 5-6

A 500 cc titanium autoclave was charged with 100 cc of aqueous alkaline composition containing a controlled concentration of thallous isobutyrate, and the autoclave was pressurized at 600 psig with an equal mixture of nitrogen and oxygen. The pressurized mixture was agitated while being heated to and maintained at a reaction temperature of 200° C. for a controlled period of time, thus permitting the oxygen gas to oxidize the thallous isobutyrate. Barium hydroxide was the alkaline material. Data relating to some preparations are shown in Table 2.

Table 2

| Code | [Tl$^+$] molarity | [Ba(OH)$_2$] molarity | pH | hrs. | % yield |
|---|---|---|---|---|---|
| Ex. 5 | 0.095 | 0.14 | 13.3 | 2 | 94 |
| Ex. 6 | 0.19 | 1.4 | 14.2 | 2 | 85 |

The thallic oxide was separated from the reaction product by filtration.

EXAMPLE 7

An aqueous solution of filtrate from the thallic oxide separation step was processed for salvaging both the isobutyric acid and the barium component. Such filtrate is transferred to a pressurized extraction apparatus in which dibutyl ether was employed to extract isobutyric acid from the aqueous system. Carbon dioxide at about 600 psig is effective in converting the soluble barium hydroxide to insoluble barium carbonate and in converting barium isobutyrate to butyric acid. Before, during, or after (preferably after) the extraction of the butyric acid, the barium carbonate precipitate is recovered from the aqueous system.

By a series of tests it was established that the organic acid recovery was manageable with acetic acid, better with propionic acid, still better with alkanoic acids having 3 or 4 carbons in the R group. Isobutyric acid has certain advantages because of its combination of advantageous partition coefficients, boiling point, and related properties. About 99 percent of isobutyric acid has been recovered from a barium bicarbonate solution by using ethyl ether as extractant for a day when the carbon dioxide pressure was essentially atmospheric pressure.

The barium carbonate is recovered, such as by filtration of the raffinate from the solvent extraction step. Such barium carbonate is calcined to generate carbon dioxide and to provide barium oxide. By dissolving the barium oxide in water an aqueous solution of barium hydroxide is prepared for recirculation to the thallic oxide preparation step.

The isobutyric acid is separated from the extractant by distillation. An aqueous solution of isobutyric acid containing about 33 percent (and assuredly between 20 percent and 45 percent) water is prepared and heated to about 110° C (and assuredly between 90° C and 150° C), which solution dissolves thallic oxide (recycled from the alkaline oxidation step). A solution of thallic triisobutyrate having a concentration within the range from 0.05 molar to 3 molar is prepared. Preferably the concentration of thallium trialkoate does not exceed 1 molar.

Such solution of thallic triisobutyrate is employed to oxidize an organic compound to a desirable partially oxidized compound, such as the oxidation of propylene to propylene oxide. Such reaction is conducted at about 70° C in a reaction mixture comprising about 70 percent tetrahydrofuran as a solvent, and the space rate is very large because the propylene is bubbled into the bottom of the reaction mixture, and the propylene oxide vapors (together with the vapors of acetone and/or other by-products) are withdrawn from the overhead.

Isobutylene glycol, ethylene glycol, cyclohexanone, and related partially oxidized organic compounds can be prepared using thallic trialkanoate as the oxidizing agent, this invention being concerned primarily with recycling components in an effort to minimize net consumption of chemicals in any use of thallium ion for oxidation to a desired partially oxidized organic compound.

Cyclohexene is oxidized to cyclohexanone in the aqueous solution of thallium triisobutyrate resulting from the leaching of thallic oxide, no tetrahydrofuran or additional water being necessary.

EXAMPLE 8

By a series of tests, the appropriate limits are established for practicing the methods of previous examples. The organic compound susceptible to oxidation may be an aldehyde, olefin, tertiary hydrocarbon (e.g., cumene), or other material which can be oxidized to a desirable partially oxidized organic compound. The concentration of thallium must be within the range from 0.05 to 3 moles per liter of aqueous system. Sufficient alkanoic acid ion, the R group of the $RCO_2$ anion having from 1 to 4 carbon atoms, must be present to justify discussion of thallium trialkanoate, but other solvents and/or anions can be present.

The desired organic product is separated from the reaction mixture, which now contains thallous alkanoate. Such thallous alkanoate composition is transferred to the alkaline oxidation zone in which the thallium ion concentration is maintained within the range from 0.05 to 3 molar. The aqueous solution of thallous alkanoate is modified by the adding of metal hydroxide to provide an aqueous composition having a pH greater than 11.9, desirably a pH of about 14.5, the concentration of hydroxyl ion preferably being about 3 molar but less than 5 molar. The metal hydroxide is desirably a soluble metal hydroxide of a metal selected from the group consisting of lithium, sodium, potassium, calcium, strontium, barium, and mixtures thereof.

The alkaline system having the pH above 11.9 and 0.5–3.0 molar thallous alkanoate is heated to a temperature within the range from 90° to 250° C. and treated with an oxygen containing gas for a few hours to convert the thallous alkanoate to thallic oxide particles of sufficient size to be separable from the alkaline system by filtration. It is surprising that filterable particles of $Tl_2O_3$ can be formed in an aqueous system having a pH higher than 11.9, inasmuch as such alkaline solutions generally favor formation of colloidal precipitates which are not readily filterable. The $Tl_2O_3$ particles are filtered (or centrifuged) from the alkaline oxidation reaction mixture, and after washing, transferred to the leaching step.

The filtrate from such $Tl_2O_3$ separation step is substantially free from thallium ion but does contain water, metal hydroxide, and metal alkanoate. Such filtrate is treated with carbon dioxide to form the metal bicarbonate and/or metal carbonate, and to form the alkanoic acid. Extraction of such carbonated system with a hydrophobic solvent such as ethyl ether or butyl ether permits separation of the alkanoic acid from the metal salt containing aqueous solution.

The metal oxide can be prepared by subjecting the metal salt to an elevated temperature at which carbon dioxide is evolved. Such step of preparing a metal oxide from a metal bicarbonate and/or metal carbonate is adequately described in prior literature and requires no further clarification. The recovered metal oxide can be dissolved in water to provide an aqueous system comprising metal hydroxide, suitable in the alkaline oxidation step.

Distillation may be employed to separate the alkanoic acid from the hydrophobic organic solvent employed as extractant. An aqueous solution containing from 20 percent to 45 percent water and from 55 to 80 percent alkanoic acid can be employed to leach thallic oxide (recirculated from the alkaline oxidation zone via a washing zone). The leaching temperature must be within the range from 90° C to 150° C. The thus prepared aqueous solution of thallic trialkanoate is recirculated to the step of preparing the desired partially oxidized organic compound. A solution containing 0.5 to 3.0 molar thallium trialkanoate is prepared.

Because the regulations governing concentrations of chemicals in waste streams are becoming more strict than in earlier decades, it is important to design chemical methods to permit recirculation of most components so that the net consumption of most chemicals is minimized. Thallium ion has been a useful research tool but it has not been used significantly for commercial oxidation of organic compounds partly because of the absence of a satisfactory method of oxidizing the thallous ion with air to prepare recoverable particles of $Tl_2O_3$, and partly because of the absence of a method of recirculating chemicals through steps such that only minimized amounts of other chemicals were consumed while oxidizing an organic compound with thallic trialkanoate.

In its broader aspects, the present invention features the method of obtaining oxygen derivatives of a suitable organic compound susceptible to oxidation to a desirable partially oxidized organic compound which method includes the steps of: treating said suitable organic compound with an aqueous solution of thallic trialkanoate to prepare a reaction product mixture containing said desirable partially oxidized organic compound and an aqueous alkanoic acid solution of thallous alkanoate, the R of the alkanoate group having from 1 to 4 carbon atoms, and the concentration of thallium ion being at least 0.05 molar but less than 3 molar; separating said desirable partially oxidized organic compound from said reaction product mixture to provide a residual aqueous alkanoic acid solution of thallous alkanoate; preparing an aqueous composition having a pH greater than 11.9, the hydroxyl ion concentration being within a range from 0.01 to 5 molar, said aqueous composition containing said residual aqueous alkanoic acid solution of thallous alkanoate, and bubbling an oxygen containing gas therethrough at a temperature within the range from 90° C. to 250° C. to prepare precipitated filterable particles of thallic oxide from the initial thallous ion content of said system, such initial thallous ion content being within the range from 0.05 molar to 3 molar and being derived from said residual aqueous alkanoic acid solution of thallous alkanoate; preparing an aqueous solution of alkanoic acid containing from 20 percent to 45 percent water and 80 percent to 55 percent alkanoic acid, said alkanoic acid being derived from said residual aqueous alkanoic acid solution of thallous alkanoate; and treating said separated thallic oxide with said aqueous solution of alkanoic acid at a temperature within the range from about 90° C. to about 150° C. to prepare a regenerated aqueous solution of thallic trialkanoate for recirculation to the treatment of additional organic compound.

I claim:
1. The method of preparing thallic oxide which consists of preparing a basic aqueous composition having a pH greater than 11.9, said basic aqueous composition containing at least 0.05 but not more than 3 molar thallous ion, said basic aqueous composition containing an amount of alkanoate ion at least approximately equal to the thallous ion, said basic aqueous composition containing sufficient metal hydroxide providing metal ion and sufficient hydroxide ion to provide said pH greater than 11.9, maintaining said basic aqueous composition at a temperature within the range from about 90° C to about 250° C, and contacting said basic aqueous composition within said temperature range with gaseous oxygen to oxidize the thallous ion to thallic ion and to form insoluble particles of thallic oxide precipitate according to the equation

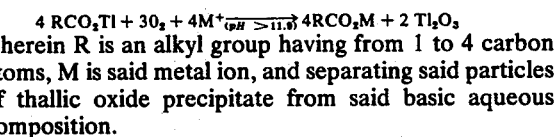

wherein R is an alkyl group having from 1 to 4 carbon atoms, M is said metal ion, and separating said particles of thallic oxide precipitate from said basic aqueous composition.

2. The method of claim 1 in which said metal hydroxide is a soluble metal hydroxide of a metal selected from the group consisting of lithium, sodium, potassium, calcium, strontium, barium, and mixtures thereof.

* * * * *